United States Patent [19]

Vaughan

[11] 4,308,215

[45] Dec. 29, 1981

[54] SULFONATION PROCESS

[75] Inventor: Ronald J. Vaughan, Orinda, Calif.

[73] Assignee: Varen Technology, Marshallton, Del.

[21] Appl. No.: 163,348

[22] Filed: Jun. 26, 1980

Related U.S. Application Data

[63] Continuation-in-part of Ser. No. 915,656, Jun. 15, 1978, abandoned.

[51] Int. Cl.$^3$ ............................................ C07C 143/24
[52] U.S. Cl. ................................ 260/505 S; 260/508; 260/509; 260/510; 260/511; 260/512 R; 260/504 R
[58] Field of Search ............ 260/505 R, 505 S, 504 R, 260/508, 509, 510, 511, 512 R

[56] References Cited

U.S. PATENT DOCUMENTS 3,976,704  8/1976  Vaughan ............................ 260/645

OTHER PUBLICATIONS

Gilbert "Sulfonation and Related Reactions" (1965) pp. 62–69.
Weininger "Contemporary Org. Chem." (1972) pp. 369, 370.

*Primary Examiner*—A. Siegel
*Attorney, Agent, or Firm*—Charles J. Tonkin

[57] ABSTRACT

A process for the sulfonation of organic compounds comprises contacting an organic compound with a sulfonating agent while the organic compound and the sulfonating agent are substantially separated by a polymeric membrane containing pendant acidic groups.

13 Claims, No Drawings

SULFONATION PROCESS

This application is a continuation-in-part of my copending application U.S. Ser. No. 915,656, filed June 15, 1978 now abandoned.

FIELD OF THE INVENTION

This invention relates to a process for the sulfonation of organic compounds with a sulfonating agent.

BACKGROUND OF THE INVENTION

Sulfonation of aromatic hydrocarbons is a commercially important process for the production of cation-exchange materials, anionic detergents, and lubricating oil additives. An example of such products is sodium dodecylbenzenesulfonate, a principal ingredient of laundry detergent formulations.

Sulfonation of the dodecylbenzene is done commercially either by heating the dodecylbenzene with 20% oleum or contacting it with vaporized sulfur trioxide.

The oleum process generally involves mixing the hydrocarbon with 20% oleum at 35°-50° C. for 2 hours. After addition of a small amount of water to separate layers, neutralization of the organic layer with sodium hydroxide yields a product of 88–90% sodium dodecylbenzenesulfonate and 10–12% sodium sulfonate. Separation and disposal of the sodium sulfate creates problems.

The processes utilizing sulfur trioxide involve lower-cost reagents and yield a product which contains less sodium sulfate. However, the reaction is very exothermic and somewhat more difficult to control. Liquid sulfur trioxide cannot be added directly to the aromatic hydrocarbon without extensive charring and dealkylation of the alkylaromatic. Normally, sulfur trioxide is used at a concentration of 5% in an inert gas such as dry air or dry nitrogen. Efficient stirring of the viscous mass is required to promote gas-liquid contact throughout the reaction mass. This is particularly difficult at the end of a batch reaction because of the extremely viscous product. Although reaction occurs readily at low temperature, a temperature of about 50° C. is used to reduce viscosity. Neutralization of the reaction mass yields a product which is substantially sodium dodecylbenzenesulfonate in aqueous solution.

Membranes of various types have been used to carry out certain separations of aqueous solutions. An example of this type of separation is the desalination of sea water by forcing it under pressure through a membrane.

It has now been found that certain membranes may be used in non-aqueous environments and under conditions which permit the selective contacting of the reagents to easily carry out reactions which hithertofore were difficult to control. This discovery provides a simple and efficient process for the sulfonation of organic compounds which avoids the problems associated with the known processes while providing a sulfonated product which is relatively free of undesirable by-products.

In my prior patent (U.S. Pat. No. 3,976,704) was described and claimed a process of nitration of organic compounds wherein the nitrating agent, usually aqueous nitric acid, and organic compound are substantially separated by a polymeric membrane preferably comprising sulfonic acid groups; when the preferred perfluorosulfonic acid polymer is used as the membrane, the sulfonic acid groups in the membrane supply the necessary catalytic acid and the organic aromatic compounds can be nitrated without the incorporation of strong sulfuric acid in the nitrating agent. Such nitration reaction inherently is in an aqueous environment not only from the water in the usual aqueous nitric acid as the nitrating agent but also from the water produced in the nitration reaction. As is well known, a catalyst is necessary in nitration to create the nitronium ion as the attacking agent in the reaction; without the catalyst the reaction does not take place. On the other hand the present sulfonation process is in a substantially anhydrous environment and the preferred sulfonating agent, sulfur trioxide, adds without generating water. As indicated above the direct contact of sulfur trioxide to an aromatic compound gives a strongly exothermic reaction and excessive formation of by-products and char; for example, direct reaction of benzene with sulfur trioxide was heretofore impractical because of excessive by-product formation; and heretofore direct contact of detergent alkylate with sulfur trioxide caused much prohibitive dealkylation. Many other differences between my patented nitration process and the present sulfonation process will be apparent to one skilled in the art.

SUMMARY OF THE INVENTION

This invention relates to a process for the sulfonation of organic compounds, especially organic aromatic compounds. The compound to be sulfonated is contacted in a substantially non-aqueous environment with an anhydrous sulfonation agent across acid polymer membranes which substantially maintain the organic compound separate from the sulfonation agent.

DETAILED DESCRIPTION OF THE INVENTION

Any organic compound capable of being sulfonated may be readily sulfonated using the process of this invention. For example, aromatic compounds are generally preferred for use in this invention, since they readily undergo sulfonation to form products that are very useful. The aromatic or aliphatic compounds which may be sulfonated using the process of this invention may be hydrocarbons or substituted derivatives thereof. The aliphatic compounds should contain at least 2 carbon atoms and preferably from 3 to 20 carbon atoms. The aromatic compounds preferably contain from 6 to 40 carbon atoms. The substituted derivatives of the aliphatic or aromatic hydrocarbons may be substituted with groups containing nitrogen, oxygen, silicon, phosphorus, sulfur and/or halogen without adversely affecting the process of this invention. For example, this process may be used to sulfonate aromatic compounds which contain one or more groups such as amino, nitroso, chloro, fluoro, bromo, silano, ether, hydroxy, and carboxy. Preferably the ratio of hydrocarbon moiety to such polar groups should be high to minimize crossing of the membrane by these substituted aromatic compounds. Control of diffusion in only one direction, i.e., sulfur trioxide permeating through to the organic reactant, can be supplemented by a pressure differential.

Because of their commercial importance, aromatic hydrocarbons are of particular interest for use in this sulfonation process. For example, linear alkylbenzenes, especially those with 10–16 carbon atoms in the alkyl group, are sulfonated for use in laundry detergents. Aromatic petroleum fractions containing alkylbenzenes, napthalenes and higher condensed aromatic systems are sulfonated for use as detergents in lubricating oils.

As indicated, the process is carried out in a substantially anhydrous environment since it is recognized that water exerts such a profound influence that sulfuric acid and free sulfur trioxide can be considered as having opposite properties as sulfonating agents. For instance, the rate of reaction of 97% sulfuric acid is slow and requires heat for reaction completion whereas the rate of reaction with sulfur trioxide is instantaneous and is exothermic throughout, the reaction readily going to completion.

Suitable diluents are those which do not prevent sulfonation. For example, sulfur trioxide may be diluted with sulfuric acid, sulfur dioxide, hydrochloric acid or boron trifluoride. If the sulfonating agent is used with a diluent, it will preferably be used at a concentration of 1 to 99%, more preferably 20 to 80%, of the sulfonating agent in the diluent. The preferred liquid sulfur trioxide can be used freshly distilled, or as the melted solid, or as the common commercial product containing an anitpolymerization stabilizer.

In this process, the organic compound is sulfonated with an anhydrous sulfonating agent. This agent can be sulfur trioxide, sulfuric acid solutions of sulfur trioxide or chlorosulfuric acid solutions of sulfur trioxide or chlorosulfuric acid which are all inherently anhydrous. Highly concentrated sulfuric acid such as at least 97% when heated becomes a solution of sulfur trioxide in sulfuric acid and hence can be used. Normally in this process a diluent is not needed but anhydrous diluents may be used, if desired, to further adjust the severity of the sulfonation reaction, particularly at the higher temperatures.

The advantages of the process of the present invention result from the use of a membrane to substantially isolate the sulfonating agent and the organic compound which is to undergo the sulfonation reaction while allowing the contacting of these two reactants across the membrane. The membrane separator for the sulfonation process must be substantially chemically inert to the action of both the organic compound and the sulfonation agent to maintain its integrity and its function as a separator. The membrane materials are preferably those capable of being fabricated into membranes having minimum thicknesses so as to obtain the conversion desired without long reaction times. Most suitable because of such properties is the preferred fluorocarbon polymers described below.

The membrane must also allow the sulfonating agent and the organic compound to come into contact at the interface formed by the membrane on a micro scale, preferably on a molecular scale, to avoid charring of the organic compound. The membrane is believed to function not as a catalyst but as a metering device controlling the flow of sulfonating agent into the organic compound. With the maximum pore size no larger than allows permeation at a rate at which the reaction heat is substantially dissipated, the sulfonating agent permeates through the membrane on a submicron scale into a relatively large mass of the organic compound, which mass acts as a heat sink. Preferably, the pore size in the membrane ranges from molecular to about 500 A, preferably below 100 A, in diameter. With such membranes, reactants come into contact on essentially the scale of reaction and the heat evolved is distributed throughout the reaction system to minimize local hot spots and loss of yield. Such a membrane provides a large surface area for reaction and mixing.

The separating membrane must be substantially impermeable to the organic compound and substantially permeable to the sulfonation agent at the temperature and conditions at which the reaction takes place. The polymeric membranes especially useful in the instant sulfonation process having the unique combination of permeability characteristics in the anhydrous reaction environment, are polymers containing acid groups, salts of acids and derivatives of acids. These polymers are known to form a semibiphasic cluster structure characterized by regions of concentrated ion groups or clusters in a matrix of fluorocarbon or hydrocarbon polymer phase. A model of ionic clustering is that the polymeric ions separate from the fluorocarbon or hydrocarbon backbone into approximately spherical clusters which are connected by short narrow channels or pores. The diameter of the ion clusters and the pores connecting the ion clusters are related to the Bragg Spacing, equivalent weight and water absorbed by the dry polymer. Low angle X-ray scans of fluorocarbon and hydrocarbon polymers containing acid groups (sulfonic, carboxylic and phosphonic) show that the average separation, Bragg spacing, of the hydrated clusters is about 50 Å for the perfluorosulfonic acid polymers, about 20 to 30 Å for the ethylene methacrylic acid copolymer. The diameter of the ion cluster ranges from about 55 Å for 950 equivalent weight to 44 Å for an 1800 equivalent weight perfluorosulfonic acid polymer. The effective pore diameter connecting the cluster network is about 16 Å for an 1100 equivalent weight and about 7 Å for a 1600 equivalent weight perfluorosulfonic acid polymer. (The difference in structure of wet and dry state of perfluorosulfonic acid resins, as indicated by X-ray scattering is shown in a paper entitled "Ionic Clustering in Nafion ™ Perfluorosulfonic Acid Membranes and Its Relationship to Hydroxyl Rejection and Chlor-alkali Current Efficiency", presented by Timothy D. Gierke at The Electrochemical Society Fall Meeting, October 1977, Atlanta, Ga.) At low equivalent weights (i.e, high concentration of acid groups) the water content in these highly swollen polymers is quite large, about 65% by weight, for an 1100 equivalent weight perfluorosulfonic acid polymer. In such swollen polymers the ion clusters are sizeable.

When the dry polymer containing sulfonic, carboxylic and phosphonic acid groups is placed in an aqueous medium, water is absorbed into the polymeric structure due to the hydrophilicity of the acid groups and forms hydration shells around the ion sites. The equilibrium water uptake is a function of the acid content and the temperature of equilibrium. In my Nitration Process (U.S. Pat. No. 3,976,704) when using the preferred perfluorosulfonic acid membrane as the separator, the membrane is swollen by the nitric acid and the permeation of benzene and other organic compounds through the membrane is primarily dependent on the solubility of the organic in the absorbed nitric acid; the membrane is saturated with nitric acid and readily permeable to the nitric acid. In the instant sulfonation process where it is essential to have an anhydrous reaction media, the membrane is not swollen by either the organic compound or the sulfonation agent. In the anhydrous state, surprisingly, the perfluorosulfonic acid membrane is substantially impermeable to the organic compound and substantially permeable to the sulfur trioxide sulfonation agent. I believe that this unique permeability characteristic results from the semibiphasic structure which is unique to halocarbon and hydrocarbon polymers containing acid groups wherein there is an ionic phase comprising clusters of ions and a halocarbon or hydrocarbon polymeric phase. In aqueous systems and systems containing polar organic compounds, the ion clusters become solvated causing swelling of the polymeric structure and permeation of water, aqueous solutions, ions, polar organics, etc. through the membrane. In an anhydrous system using sulfur trioxide, the polymeric structure is not swollen and the ionic sites are not solvated to effect permeation. Since I have found that the rate of sulfonation is highest with the polymeric membranes of highest acid content, it appears that the sulfur trioxide permeates through the ion clusters and interconnecting pores of the membrane essentially on a molecular scale (or at least on a submicron scale). And, the fluorocarbon and ionic phases are substantially impermeable to the organic compound being sulfonated.

Thus, the acid copolymer membranes generally useful in this invention are substantially chemically inert to the action of both the organic compound and the sulfonating agent and have interconnecting pores of submicron size (preferably from molecular to 100 Å) so that permeation of the sulfonating agent through the membrane to the bulk of the organic compound is not a rate greater than that at which under the reaction conditions the heat evolved is substantially dissipated. Membrane materials of the desired chemical inertness, submicron porosity and ionic permeable channels, in addition to the preferred fluorocarbon polymers described below, can be selected from those described by Gregor U.S. Pat. No. 3,808,305 (crosslinked polyvinylidene fluoride) and McKelvey et al U.S. Pat. No. 3,132,094 (polyvinyl fluoride-acrylonitrile). Hydrocarbon acid copolymers such as methacrylic-ethylene polymers (including commercial "Surlyn" polymer) may also be used since they would be expected to retain their physical integrity even though at higher temperatures with sulfur trioxide there may be some sulfonation of the copolymer.

The preferred fluorocarbon polymers are perhalocarbon polymers having no hydrogen atoms on the polymeric backbone. The carbon backbone is substituted only by (1) chloro and/or fluoro groups with a maximum of 25 percent by weight of chlorine groups and (2) pendant acid groups selected from sulfonic acid, carboxylic and phosphonic acid groups or mixtures thereof. The preparation of such materials, e.g., "Kel-F" modified with the above-mentioned acid groups is well known in the art. (See, for example, Hiroshi Ukihashi in Chemtech, February 1980, pp. 118–120. Similar "Kel-F" type materials are described in Chen et al U.S. Pat. No. 3,257,334.)

The membrane is preferably a fluorocarbon polymer having pendant acid groups such as carboxylic, phosphonic and especially sulfonic as in perfluorocarbonsulfonic acid polymer, such as is described in U.S. Pat. Nos. 3,041,317; 3,282,875 and 3,624,053, the disclosures of which are hereby incorporated by reference. These materials are preferred because of their inertness to the reactants at the conditions at which the reaction is taking place, and ease of fabrication into suitable membranes. A particularly preferred membrane material is a copolymer of tetrafluoroethylene and a perfluorovinyl ether having pendant sulfonic acid groups. An example of such a membrane material is Nafion ™ resin, available from E. I. duPont and Co.

The perfluorocarbonsulfonic membrane may be utilized in the form of sheets, tubes and hollow fibers. The material may be laminated to scrim to allow for more dimensional stability. The material may be incorporated into the diffusion cell by supported or unsupported means; for example, when hollow fibers are utilized other than at the point where a hollow fiber enters and exits from the diffusion cell there is no need, in general, for support. When the membrane material is present as a sheet, it may be supported on a stainless-steel screen, on a porous metal surface, or on an inert fabric material which allows free passage of both reactants and products.

It has been found that when the preferred perfluorinated sulfonic acid polymer is used as the membrane that the equivalent weights of the polymer have an important effect on the rate of conversion; that is, it has been found that the use of the lower equivalent weights of the polymer, every other variable being equal, results in increased reaction rates. Equivalent weights is defined as the weight of the membrane polymer per mole of sulfonic acid groups in grams. Equivalent weights in the range of 900 to 1700 are generally preferred. It has been found that weights as low as 1060 give optimum results, while the higher weights, that is 1340 and above, show decreased conversions. The practical minimal equivalent weight which may be used in these polymers is about 700. At weights below this, difficulties arise in fabrication and mechanical properties of fluorinated sulfonic acid polymer films, hollow fibers, tubes, etc.

The process of the present invention may be conveniently carried out in a diffusion cell which comprises a chamber which is divided into separate compartments by means of a membrane. Each compartment will have means for removing its contents therefrom. The process may be carried out continuously or batchwise, but preferably in a continuous manner.

The membrane may be utilized in various shapes and thicknesses; for example hollow fibers, tubes, planar-shaped, etc., membranes may be placed in a diffusion cell so as to form the separate compartments. The membrane may vary in thickness from 0.0001 to 0.040, preferably from 0.001 to 0.10, inch. The thickness of the membrane will be chosen with a view toward ease of fabrication and maintenance in an integral form during the process of the present invention.

The organic compound which is present as a liquid, i.e., either in solution or neat, is contacted with the agent in a countercurrent or concurrent manner.

The contacting of the organic compound and the sulfonation agent may be varied by means well known to those skilled in the art to obtain various degrees of conversion per pass. In general, longer times of contact and decreased membrane thicknesses promote increased conversion. The temperature at which the contact takes place substantially affects the degree of conversion. That is, as the temperature increases, so does the degree of conversion. The time of contact of the sulfonation medium with the organic compound may be varied by either decreasing the flow rate or increasing the size or area of contact in the diffusion cell.

The material which is to undergo sulfonation, if a liquid, is preferably used neat so as to minimize any undesirable side reactions with a solvent. The material, if a solid at room temperature, may be heated to a temperature at which it may be sulfonated as a melt. For example, the sulfonation process may take place at temperatures of up to 200° C. Thus, materials which are molten and substantially fluid at temperatures up to this limit may be utilized.

Materials which cannot be fluidized by temperature can be dissolved in a suitable solvent and used in this manner. The use of a solvent is generally more preferable than heating to high temperatures to fluidize a solid reactant. It is, of course, obvious to the skilled artisan that the solvent will have to be selected so as to minimize any interference with the sulfonation agent and/or the membrane material at the temperatures of reaction. The solvent also should be immiscible with the sulfonation agent so as to maintain the phase separation which provides one of the advantages of the present process. Examples of suitable solvents include nitrobenzene, dichlorobenzene, cyclohexane, $CCl_4$, etc.

The process of the present invention may be carried out at reaction conditions which are similar to the prior art processes; that is, the temperature at which the sulfonation process may be run varies from the freezing point of either the organic compound or the sulfonation medium or the mixture of organic compound and solvent, if used, and the boiling point of any of the components at the pressures employed. Thus, the process may be carried out over broad temperature and pressure ranges. It has been found that increasing the temperature increases the conversion rate. However, the upper limit depends on the interference of competitive reactions and inertness of the membrane material to temperature. It has been found that when using the process of the present invention, unlike the prior art, competing reactions are minimized. Thus, it is possible to go to higher temperatures and achieve greater rates of conversion with the present process than with the prior art processes.

EXAMPLES

The following examples are presented for the purposes of illustrating the invention and should not in any way be interpreted as limiting the scope of the invention.

Nafion perfluorosulfonic acid membranes were obtained as unreinforced sheets and tubes from E. I. duPont de Nemours and Co. Membrane equivalent weights (expressed as grams polymer per sulfonic acid group with the polymer equilibrated with atmospheric humidity) were supplied by DuPont. Membrane tubing used was 0.024" I.D. and 0.036" O.D. Sheet membranes were 0.004" thick. The membranes were cleaned and regenerated by contact with 70% nitric acid at 80°–100° C. followed by extensive washing in distilled water and drying at 80°–100° C. in a stream of dry nitrogen. Static sulfonations were conducted in two-compartment, 316-stainless-steel cells comprising two mating circular halves of identical cavity dimensions 0.6×3.7 cm diameter separated by an unreinforced sheet membrane clamped between the two halves. After assembly, the cells were placed on a shaking platform immersed in a water bath and allowed to come to temperature with the dodecylbenzene in one compartment. Reaction commenced with addition of liquid sulfur trioxide to the other compartment. Samples were removed at intervals and measured for detergent content.

Continuous flow sulfonations were conducted in an annular tube reactor comprising an inner tube of the membrane and an outer tube of FEP-Teflon® (⅛" O.D.×1/16" I.D.) with Swagelok® end fittings arranged in a heat-exchange configuration. Either the dodecylbenzene or the sulfur trioxide was introduced through the inner (membrane) tube and the other reactant was introduced into (and withdrawn from) the annular shell between the two tubes. The coiled reactor was immersed in a stirred reaction kettle of distilled water maintained at the desired temperature by a thermistor temperature controller. Back pressure was produced on the hydrocarbon flow by means of a check valve of adjustable cracking pressure. A metering valve was fitted to the exit of the sulfur trioxide flow. Dodecylbenzene flow was provided by a calibrated constant-displacement piston pump fitted with a 25 psig cracking-pressure check valve on the outlet. A pressure gauge was on a tee between the pump and the inlet to the reactor. Sulfur trioxide flow was provided by a pressurized reservoir containing the liquid fitted with a pressure gauge above the liquid and an exit metering valve. The pressurized reservoir and lines leading to the reactor were contained inside an oven maintained at 35°–40° C. to keep the sulfur trioxide molten.

Dodecylbenzene (Nalkylene 500), tridecylbenzene (Nalkylene 600), "C560" (a 50% slurry of sodium dodecylbenzene sulfonate) and 97% dodecylbenzenesulfonic acid were obtained from Conoco Chemicals. The linear detergent alkylate consists of a mixture of isomers in which the benzene ring may be attached to the linear $C_{12}$ (or $C_{13}$) chain at any of the interior carbons. Sulfur trioxide (Sulfan B, with stabilizer) and 20% oleum (fuming sulfuric acid) were products of Baker and Adamson.

Detergent content was measured by means of a modified methylene-blue phase transfer method [Longwell and Manviece, Chem. Abstr. 78, 2690]b; Kolthoff, Elving, Strauss, *Treatise on Anal. Chemistry* III, Vol. I, p. 439):

Samples (typically 30–100 mg) from the sulfonation were weighed into test tubes and diluted with 5.0 ml of 95% ethanol. An aliquot (0.002–0.005 ml) of this solution was further diluted in a 13×100 mm test tube with 2.0 ml of aqueous methylene blue solution [$KH_2PO_4$ (10 g), 10% $H_2SO_4$ (14 ml), 0.0203 g methylene blue, dissolved to one liter] and 3.0 ml of reagent-grade chloroform. The tube contents were mixed vigorously on a "vortex mixer", and centrifuged to clarify the layers. The absorbance of the methylene blue-detergent complex in chloroform was read at 650 nm and compared to a blank and standards prepared from dodecylbenzenesulfonic acid (97%) and sodium dodecylsulfate.

EXAMPLE 1

Static sulfonation of dodecylbenzene with $SO_3$: Effect of membrane equivalent weight Sheet membranes of different equivalent weight but similar fabrication were obtained and assembled into 3 identical 316-stainless-steel cells. The cells were filled on one side with dodecylbenzene (Nalkylene 500) and placed on a shaking platform in a water bath at 40° C. Reaction commenced on addition of liquid sulfur trioxide to the other side. Samples were withdrawn by syringe from the hydrocarbon side at intervals and analyzed for detergent content by the "methylene blue" method. The results are in Table I. Higher equivalent weight appears to lead to slower conversion, though it has little effect on the final percent conversion. The higher proportion of sulfonic acid groups in the lower equivalent weight polymer probably increases the permeation rate of the sulfur trioxide. The decrease in detergent content at long reaction times (particularly evident in the 1100 equivalent weight sample) is attributed to the formation of higher sulfonated products in the presence here of excess sulfur trioxide; these products would not undergo phase transfer with methylene blue as readily as the monoanions.

Table I shows static sulfonation in two-cavity membrane cells with membranes (4 mil thickness) of different equivalent weight. Temperature (T) was 40° C. The equivalent weight (E.W.) is equivalent weight of membrane polymer. Duplicate analysis of percent detergent by weight (97% AB sulfonic acid standard).

TABLE I

| Time (Hr.) | 1100 E.W. | 1200 E.W. | 1340 E.W. |
|---|---|---|---|
| 0–0.1 | 0.2 | 0.1 | 0 |
| 0.5 | 12.6 | 4.5 | 0.5 |
| 0.6 | 12.4 | — | — |
| 1.0 | 33.9 | 19.1 | 12.3 |
| 1.2 | 37.5 | — | — |
| 2.0 | 46.7 | 33.5 | 24.1 |
| 2.2 | 48.4 | — | — |
| 4.0 | — | 41.9 | 41.8 |
| 4.5 | 62.6 | — | — |
| 5.9 | — | 63.0 | 47.9 |
| 6.2 | 74.0 | — | — |
| 22.5 | 67.6 | 85.6 | 86.9 |

EXAMPLE 2

Sulfonation of dodecylbenzene in annular tube reactor

Sulfur trioxide was introduced into the inner (membrane) tube and dodecylbenzene (Nalkylene 500) was introduced into the annular shell of an annular tube reactor (22 ft., 0.024 in. I.D., 0.0045 in. wall, 1340 E.W. membrane) maintained at 60° C. Dodecylbenzene flow was maintained constant and samples were collected at intervals after steady state was established and analyzed for detergent content. In one run (Table IIA), the sulfur trioxide pressure was maintained (from the reservoir) in the membrane tube; however, no sulfur trioxide was allowed to bleed through the reactor. In a second run (Table IIB), a fairly steady bleed of 2.3 ml/hr of sulfur trioxide was allowed to exit from the reactor.

Table IIA shows sulfonation of dodecylbenzene by $SO_3$ in annular tube reactor (22', 1340 E.W.), no $SO_3$ bleed. Temperature was 60° C., dodecylbenzene flow 0.20 ml/min at 35–38 psig, $SO_3$ pressure 38 psig.

TABLE IIA

| Sample No. | Time of Sample (hr) | % Detergent |
|---|---|---|
| 1 | (0) | 63.1 |
| 2 | 1.1 | 57.9 |
| 3 | 2.0 | 12.4 |
| 4 | 2.5 | 4.7 |
| 5 | 3.0 | 6.4 |
| 6 | 3.5 | 14.0 |
| 7 | 4.0 | 17.8 |

Table IIB is the same as Table IIA, except with $SO_3$ bleed 2.3 ml/hr (33 psig); dodecylbenzene flow 0.10 ml/min (38–40 psig).

TABLE IIB

| Sample No. | Time of Sample (hr) | % Detergent |
|---|---|---|
| 1 | (0) | 60.3 |
| 2 | 0.5 | 75.3 |
| 3 | 1.0 | 64.9 |
| 5 | 2.0 | 51.7 |
| 6 | 2.5 | 69.9 |
| 7 | 3.0 | 68.2 |
| 8 | 3.5 | 66.8 |
| 9 | 4.0 | 53.7 |

Although there is some variance in the results, they indicate that the reaction shows considerably with time in the absence of continuing $SO_3$ bleed, suggesting accumulation of an inhibitor. The inhibition shown in Table IIA was completely removed by quickly flushing the reactor with $SO_3$; cessation of $SO_3$ flow again caused increasing inhibition of the sulfonation with time. The lack of reaction of the system with 20% oleum as the sulfonating agent at this temperature (below) suggests that sulfuric acid may be the inhibitor, formed from traces of water in the system and side reactions (e.g., anhydride, sulfone formation) which produce water as product.

EXAMPLE 3

Sulfonation of tridecylbenzene with 20% oleum in annular tube reactor

Tridecylbenzene (Nalkylene 600) was introduced into the inner (membrane) tube (0.095 ml/min) and Oleum (fuming sulfuric acid containing 20% sulfur trioxide) was introduced into the annular channel (0.10 ml/min) of a 22' annular tube reactor (1340 E.W.) The reactor was maintained at constant temperature by a forced-fan oven. Samples were collected from both effluents after at least one reactor volume had passed through at the desired temperature. Neutralization and analysis of the oleum samples revealed no detectable (<0.1%) detergent. The results for tridecylbenzene effluent are presented in Table III, which shows sulfonation of tridecylbenzene (Nalkylene 600) with 20% oleum in annular tube reactor.

TABLE III

| Sample No. | Temp., °C. | % Detergent |
|---|---|---|
| 1 | 61 | 0 |
| 2 | 81 | 0 |
| 3 | 101–102 | 0.1 |
| 4 | 110–111 | 6.5 |
| 5 | 119–120 | 21.2 |

Temperatures much higher than necessary for the sulfur trioxide sulfonation are required for sulfonation with 20% oleum, suggesting that the presence of sulfuric acid may well inhibit the reaction with sulfur trioxide. However, this method of sulfonation does give reasonable sulfonation of tridecylbenzene, without the introduction of large quantities of sulfuric acid into the hydrocarbon. Higher concentrations of sulfur trioxide relative to sulfuric acid (e.g., 50% oleum) thus will be preferred sulfonating agents of activity intermediate between sulfur trioxide and sulfuric acid when a lesser degree of activity is required to moderate the reaction.

Example 4

Sulfonation of dodecylbenzene with $SO_3$ in annular tube reactor—effect of temperature and $SO_3$ differential pressure The reactor of Example 2 was run with a differential pressure of approximately 10 psig across the membrane to increase the rate of SO₃ diffusion and with a bleed of SO₃ through the reactor (T=60° C., SO₃ 52-53 psig, dodecylbenzene 40-42 psig at 0.10 ml/min). The measured detergent concentration in the hydrocarbon effluent increased to 90.1%. Increasing the temperature at 70° C. under these conditions increased the detergent concentration in the hydrocarbon effluent to 95.3%.

Example 5

Preparative demonstration

Sulfur trioxide was introduced into the inner tube (1340 E.W.) at 47 psig) and dodecylbenzene (0.12 ml/min, 35-40 psig) was introduced into the annular channel of a 20' annular tube reactor at 60° C. with a slow SO₃ bleed. Samples of 4-5 were collected and analyzed for detergent content. The pooled samples #3-8 (25.8 g) (Table V) were again analyzed for detergent content (75.0%), then neutralized with 45% sodium hydroxide (to pH 10) and extracted with two 75-ml portions of n-pentane to remove unreacted dodecylbenzene. Evaporation of solvent yielded 3.2 g of material with infrared spectrum identical to starting dodecylbenzene. The aqueous layer (containing the sodium dodecylbenzene sulfonate) was evaporated to a moist paste, which was extracted with 3 portions (125 ml each) of absolute ethanol, leaving a light tan precipitate which was dried and weighed (10.1 g). The combined ethanol extracts were dried under vacuum to yield 14.05 g of slightly moist sodium dodecylbenzenesulfonate (identical in infrared spectra to a sample prepared in like manner from 97% dodecylbenzene sulfonic acid (Conoco). Analysis of the detergent content (19.1%) of the ethanol insoluble precipitate and the isolated sodium dodecylbenzenesulfonate (94.5%) were performed and indicated a high degree of separation in the isolation. The infrared spectrum of the precipitate indicated a modest organic content; it was identical to the infrared spectrum of a precipitate isolated by the same procedure from the commerical 97% sulfonic acid.

TABLE V

| Sample No. | Collection time start (hour) of fraction | Wt (g) | % Detergent |
|---|---|---|---|
| 1 | 0 | 4.6 | 41.2 |
| 2 | 0.7 | 5.1 | 68.0 |
| 3 | 1.3 | 5.1 | 83.4 |
| 4 | 2.0 | 5.2 | 77.7 |
| 5 | 2.7 | 4.9 | 68.8 |
| 6 | 3.3 | 4.9 | 70.6 |
| 7 | 4.0 | 3.5 | 72.8 |
| 8 | 4.7 | 5.7 | 73.7 |
| 9 | 5.3 | 4.3 | 58.3 |
| 10 | 6.0 | 3.8 | 58.5 |
| 11 | 6.7 | 4.3 | 54.9 |
| 12 | 7.3 | 2.6 | 61.1 |

What is claimed is:

1. In the process for the sulfonation of organic compounds by contacting the organic compounds with a sulfonating agent selected from sulfur trioxide, a solution of sulfur trioxide in sulfuric acid and chlorosulfonic acid, the improvement comprising maintaining the sulfonating agent and the organic compound in a substantially non-aqueous environment and substantially separated by means of an acid polymer membrane which is substantially chemically inert to the action of both the organic compound and the sulfonating agent and which in said substantially non-aqueous environment is substantially impermeable to said organic compound and substantially permeable to said sulfonating agent.

2. The process of claim 1 wherein said membrane is a perhalocarbon polymer having pendant carboxylic, phosphonic or sulfonic acid groups or mixtures thereof.

3. The process of claim 1 wherein said sulfonating agent is sulfur trioxide or a solution of sulfur trioxide in sulfuric acid.

4. The process of claim 1 wherein the active ingredient in the sulfonating agent is sulfur trioxide.

5. The process of claim 2 wherein said organic compound is an alkylbenzene.

6. The process of claim 5 wherein said alkyl group contains from 10 to 16 carbon atoms.

7. The process of claim 2 wherein said organic compound is an oil-soluble aromatic hydrocarbon.

8. The process of claim 2 wherein said membrane is a perfluorocarbonsulfonic acid polymer having an equivalent weight of 900 to 1700.

9. The process of claim 8 wherein said membrane is a copolymer of tetrafluoroethylene and perfluorovinyl ether having pendant sulfonic acid groups.

10. The process of claim 5 wherein said organic compound is dodecylbenzene or tridecylbenzene.

11. The process of claim 1, wherein said acid polymer membrane has a maximum pore size no larger than allows permeation of said sulfonating agent at a rate at which the reaction heat is substantially dissipated.

12. The process of claim 11, wherein said acid polymer membrane has a maximum pore size of 500 Å.

13. The process of claim 4, wherein a portion of said sulfur trioxide on the sulfonating agent side of said membrane is at least periodically removed to reduce the accumulation of reaction inhibitors.

* * * * *